(12) United States Patent
Hirata

(10) Patent No.: US 10,977,488 B2
(45) Date of Patent: Apr. 13, 2021

(54) LINE-OF-SIGHT DIRECTION CALIBRATION DEVICE, LINE-OF-SIGHT DIRECTION CALIBRATION METHOD, AND LINE-OF-SIGHT DIRECTION CALIBRATION PROGRAM

(71) Applicant: Mitsubishi Electric Corporation, Tokyo (JP)

(72) Inventor: Takahisa Hirata, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 16/915,264

(22) Filed: Jun. 29, 2020

(65) Prior Publication Data
US 2020/0327324 A1    Oct. 15, 2020

Related U.S. Application Data

(63) Continuation of application No. PCT/JP2018/000091, filed on Jan. 5, 2018.

(51) Int. Cl.
*H04N 7/18* (2006.01)
*G06K 9/00* (2006.01)
*G06F 3/01* (2006.01)

(52) U.S. Cl.
CPC ......... *G06K 9/00604* (2013.01); *G06F 3/013* (2013.01); *G06K 9/00214* (2013.01)

(58) Field of Classification Search
CPC ............ G06K 9/00604; G06K 9/00214; G06F 3/013; A61B 3/113; G01B 21/22
See application file for complete search history.

(56) References Cited

U.S. PATENT DOCUMENTS

2011/0169625 A1* 7/2011 James ............... G08G 1/166
                                                       340/439
2012/0008092 A1* 1/2012 Eberl ............... G02B 27/0093
                                                       351/206
(Continued)

FOREIGN PATENT DOCUMENTS

JP    2000-308618 A    11/2000
JP    2008-243031 A    10/2008
(Continued)

OTHER PUBLICATIONS

Chen et al, Real time eye detection and event identification for human computer interactive control for driver assistance (Year: 2014).*

(Continued)

*Primary Examiner* — Shan E Elahi
(74) *Attorney, Agent, or Firm* — Birch, Stewart, Kolasch & Birch, LLP

(57) ABSTRACT

Included are: a calibration information acquiring unit for acquiring three-dimensional coordinates for at least one gaze target for calibration, the three-dimensional coordinates indicating a position of each gaze target for calibration; a sample acquiring unit for acquiring multiple samples indicating a line-of-sight direction of a user; a calibration model generating unit for generating multiple calibration models indicating three-dimensional coordinates that are candidates for a position of the user on the basis of the three-dimensional coordinates indicating a position of each of the gaze targets for calibration and the samples indicating the line-of-sight direction of the user gazing at each of the gaze targets for calibration; and a calibration parameter calculating unit for calculating calibration parameters on the basis of the generated calibration models.

9 Claims, 9 Drawing Sheets

(56) References Cited

U.S. PATENT DOCUMENTS

| | | | |
|---|---|---|---|
| 2014/0267415 A1* | 9/2014 | Tang | G08G 1/166 345/633 |
| 2016/0066782 A1 | 3/2016 | Kimura et al. | |
| 2016/0327813 A1 | 11/2016 | Baranton et al. | |
| 2018/0267323 A1 | 9/2018 | Tsurumi | |
| 2019/0164330 A1* | 5/2019 | Sugano | G02B 27/0172 |

FOREIGN PATENT DOCUMENTS

| | | |
|---|---|---|
| JP | 2010-30361 A | 2/2010 |
| JP | 2012-217524 A | 11/2012 |
| JP | 2014-52758 A | 3/2014 |
| JP | 2014-226377 A | 12/2014 |
| JP | 2016-539363 A | 12/2016 |
| WO | 9-238905 A | 9/1997 |
| WO | WP 2015/136908 A1 | 9/2015 |
| WO | WO 2016/129156 A1 | 8/2016 |

OTHER PUBLICATIONS

Wang et al, Driver gaze tracker using deformable template matching (Year: 2011).*
International Search Report, issued in PCT/JP2018/000091, PCT/ISA/210, dated Apr. 3, 2018.

* cited by examiner

LINE-OF-SIGHT DIRECTION CALIBRATION DEVICE, LINE-OF-SIGHT DIRECTION CALIBRATION METHOD, AND LINE-OF-SIGHT DIRECTION CALIBRATION PROGRAM

CROSS REFERENCE TO RELATED APPLICATIONS

This application is a Continuation of PCT International Application No. PCT/JP2018/000091 filed on Jan. 5, 2018, which is hereby expressly incorporated by reference into the present application.

TECHNICAL FIELD

The present invention relates to technology for calibrating a measured line-of-sight direction of a person.

BACKGROUND ART

In recent years, it is expected to utilize a measured line-of-sight direction of a person in various fields. For example, utilization in driving assistance for drivers of vehicles includes determining the recognition state of a driver toward the surroundings such as the degree of attention to pedestrians or the like or inattentive driving on the basis of a measured line-of-sight direction of the driver, or displaying assistance information in the line-of-sight direction.

Generally, the measured line-of-sight direction includes a measurement error. Therefore, in a case where a measured line-of-sight direction is used, technology for calibrating a measurement error included in the measured line-of-sight direction is also used in combination.

Patent Literature 1 describes a line-of-sight direction measurement device that extracts a corneal reflection image from each of the driver's eyes from images captured by two cameras, detects the eyeball positions having the center between the eyeballs at the intersection of two straight lines connecting coordinates of the two corneal reflection images and the focal points of the corresponding cameras to detect the rotation angles of the eyeballs with respect to the imaging direction of the cameras, and calculates the line-of-sight direction on the basis of the detected eyeball positions and the rotation angle of the eyeballs. The line-of-sight direction measurement device described in Patent Literature 1 starts calibration operation when a specific device such as a navigation device is operated by an occupant, and calculates a correction coefficient that matches the line-of-sight direction of the driver calculated as described above with a straight line passing through the center of the eyeballs and a specific device.

CITATION LIST

Patent Literature

Patent Literature 1: JP H09-238905 A

SUMMARY OF INVENTION

Technical Problem

However, in the line-of-sight direction measurement device in Patent Literature 1 described above, only a correction coefficient for a line-of-sight direction that is measured with respect to a line of sight directed to the specific device is calculated as a calibration amount for calibration of a measurement error. Therefore, there is a problem that the calibration amount cannot be calculated for a line of sight directed to any point other than the specific device.

The present invention has been made to solve the above-described problem, and an object of the invention is to calculate a calibration amount for calibration of a measurement error included in a line-of-sight direction measured for a line of sight directed to any point.

Solution to Problem

A line-of-sight direction calibration device according to the present invention includes: a calibration information acquiring unit for acquiring three-dimensional coordinates for at least one gaze target for calibration, the three-dimensional coordinates indicating a position of each gaze target for calibration and being based on a predetermined coordinate system; a sample acquiring unit for acquiring multiple samples indicating a line-of-sight direction of a user, the multiple samples being based on an unknown coordinate system that does not have a correspondence relationship with the predetermined coordinate system; a calibration model generating unit for generating multiple calibration models indicating three-dimensional coordinates that are candidates for a position of the user on a basis of the three-dimensional coordinates acquired by the calibration information acquiring unit, the samples indicating the line-of-sight direction of the user gazing at each of the gaze targets for calibration, acquired by the sample acquiring unit, an unknown parameter indicating the correspondence relationship between the predetermined coordinate system and the unknown coordinate system; and a calibration parameter calculating unit for calculating, as a calibration parameter, the unknown parameter and the position of the user on a basis of the calibration models generated by the calibration model generating unit.

Advantageous Effects of Invention

According to the present invention, it is possible to calculate a calibration amount for calibrating a measurement error included in a line-of-sight direction measured for a line of sight directed to any point.

DESCRIPTION OF EMBODIMENTS

To describe the present invention further in detail, an embodiment for carrying out the present invention will be described below with reference to the accompanying drawings.

First Embodiment

Figure 1:
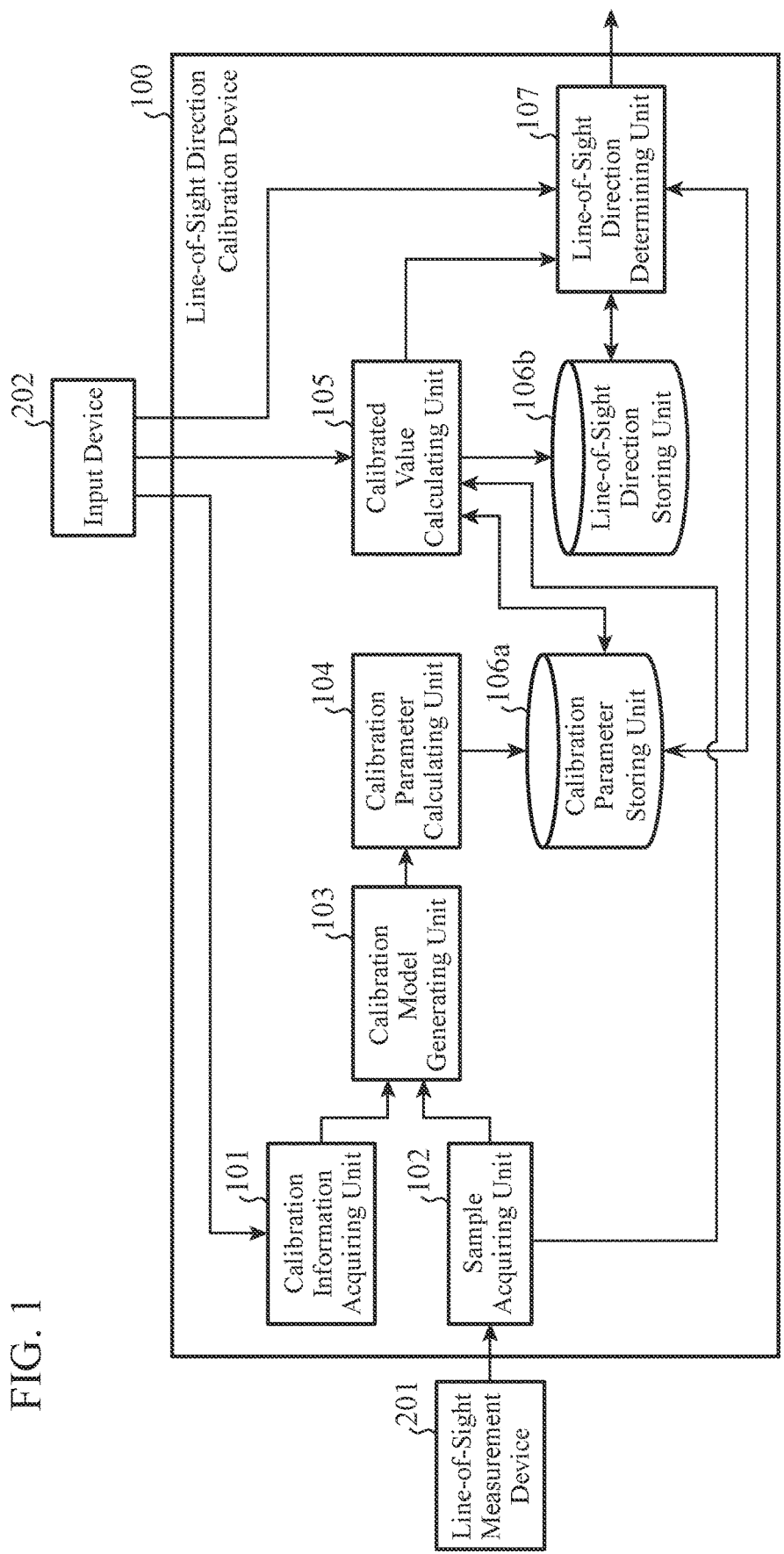
FIG. 1 is a block diagram illustrating a configuration of a line-of-sight direction calibration device according to a first embodiment.

FIG. 1 is a block diagram illustrating a configuration of a line-of-sight direction calibration device 100 according to a first embodiment.

The line-of-sight direction calibration device 100 includes a calibration information acquiring unit 101, a sample acquiring unit 102, a calibration model generating unit 103, a calibration parameter calculating unit 104, a calibrated value calculating unit 105, a calibration parameter storing unit 106a, a line-of-sight direction storing unit 106b, and a line-of-sight direction determining unit 107.

The line-of-sight direction calibration device 100 is also connected with a line-of-sight measurement device 201 and an input device 202.

The line-of-sight direction calibration device 100 can be widely applied to cases where a relative position between a gaze target for calibration and a user is assumed to be fixed, such as calibration of a measured line-of-sight direction of an occupant in a vehicle or calibration of a line-of-sight direction measured for a user who visually recognizes a display on a desk or a display secured to the user's head.

The calibration information acquiring unit 101 acquires three-dimensional coordinates of a preset gaze target that a user is to gaze at (hereinafter referred to as a gaze target for calibration) for generation of a calibration model described later. Here, a user is a person whose line of sight is to be measured. The calibration information acquiring unit 101 acquires the three-dimensional coordinates of the gaze target for calibration from an internal storage device. Alternatively, the calibration information acquiring unit 101 acquires three-dimensional coordinates indicating the position of the gaze target for calibration from an external program via the input device.

As for the number of gaze targets for calibration, any number of objects may be set that can satisfy at least the degree of freedom of calibration. For example, let us assume that the line-of-sight direction calibration device 100 is used in a vehicle and that in a case where the line-of-sight direction of a driver of the vehicle is calibrated, a rotation parameter ($\rho$ in equation (1) described later), which indicates an angle formed by a reference direction for measurement of the line-of-sight direction and a calibration reference direction is known in advance, is fixed and is known in advance, and that the position of the driver's seat in the left-right direction (an x component of $x_{target}$ in equation (1)) is fixed and is known in advance. In this case, the degree of freedom of calibration includes two degrees of freedom in the front-rear direction and the up-down direction of the user position (y and z components of $x_{target}$ in equation (1)). Further assuming that the line-of-sight measurement device 201 provides the yaw direction and the pitch direction of a line of sight, a measurement value with two degrees of freedom can be obtained, and thus it suffices to set at least one gaze target for calibration. In the following description, a case will be described as an example where the rotation parameter ($\rho$) is unknown and there are multiple gaze targets for calibration. Note that the accuracy of calculated calibration parameters generally improves as the number of gaze targets for calibration increases.

While the line-of-sight direction calibration device 100 is calculating calibration parameters, the sample acquiring unit 102 acquires multiple samples indicating line-of-sight directions of the user who is gazing at each gaze target for calibration. The sample acquiring unit 102 acquires multiple line-of-sight directions for a user who is gazing at one gaze target for calibration. The sample acquiring unit 102 also acquires a line-of-sight direction for the user who is gazing at each of multiple gaze targets for calibration.

Note that it is desirable that, most simply, the reference of a line-of-sight direction, that is, the true line-of-sight direction at the zero point of the line-of-sight measurement device 201 is parallel to the front direction of the user. However, in a case where the reference of the line-of-sight direction is included in calibration targets, the reference of the line-of-sight direction may be unknown. In this case, a calibrated line-of-sight direction is calculated on the basis of a desirably designated azimuth, for example, a Y axis described later, by a calibrating process described later. The sample acquiring unit 102 outputs the acquired samples to the calibration model generating unit 103.

Meanwhile, while the line-of-sight direction calibration device 100 is performing a line-of-sight direction calibrating process and a line-of-sight direction determining process using the calibration parameters, the sample acquiring unit 102 acquires a sample indicating the user's current line-of-sight direction. The sample acquiring unit 102 outputs the acquired sample to the calibrated value calculating unit 105.

The calibration model generating unit 103 generates multiple calibration models indicating three-dimensional coordinates that are candidates for the user position by associating the three-dimensional coordinates of the gaze target for calibration acquired by the calibration information acquiring unit 101 with the samples acquired by the sample acquiring unit 102. Note that the calibration model generating unit 103 may acquire multiple samples stored in association with information indicating the gaze target for calibration in cooperation with an external program. The user position corresponds to, for example, the center position of the user's head, the center position of the eyeballs, or the center position between the eyebrows. The calibration model generating unit 103 outputs the generated calibration model to the calibration parameter calculating unit 104. Note that detailed contents of the process of the calibration model generating unit 103 will be described later.

The calibration parameter calculating unit 104 calculates calibration parameters on the basis of the calibration model generated by the calibration model generating unit 103. The calibration parameter calculating unit 104 stores calibration parameters in the calibration parameter storing unit 106a.

Note that detailed contents of the process of the calibration parameter calculating unit 104 will be described later.

The calibrated value calculating unit 105 calculates a calibrated line-of-sight direction on the basis of the calibration parameters calculated by the calibration parameter calculating unit 104. For example, the calibrated value calculating unit 105 accepts, via the input device 202, a request from an external program to determine whether or not the user is visually recognizing a desired gaze target (hereinafter referred to as a gaze determination target). Upon receiving the request, the calibrated value calculating unit 105 acquires a sample indicating the current line-of-sight direction from the sample acquiring unit 102. The calibrated value calculating unit 105 calibrates the line-of-sight direction using the calibration parameters stored in the calibration parameter storing unit 106a. The calibrated value calculating unit 105 outputs the calibrated line-of-sight direction to the line-of-sight direction determining unit 107.

The calibrated value calculating unit 105 may further store the calibrated line-of-sight directions in the line-of-sight direction storing unit 106b at all times. In this case, the line-of-sight direction calibration device 100 returns, to an external program that intends to determine whether or not the user is visually recognizing the gaze determination target, values obtained by converting the three-dimensional coordinates of the gaze determination target into a calibrated line-of-sight direction, for example, $\theta_{target}$ in a determining process described later. The external program independently performs a determining process by referring to the line-of-sight direction storing unit 106b as needed and comparing it with the calibrated line-of-sight direction. Note that the combination of calibrated values stored in the line-of-sight direction storing unit 106b and the calibration parameters provided to the external program is an example, and can be modified as needed depending on the determining process.

The line-of-sight direction determining unit 107 determines whether or not the user is visually recognizing the gaze determination target on the basis of the calibration parameters stored in the calibration parameter storing unit 106a and the line-of-sight direction calibrated by the calibrated value calculating unit 105.

The line-of-sight direction determining unit 107 determines that the user is visually recognizing the gaze determination target for example when the calibrated line-of-sight direction is similar to the direction of the gaze determination target. The line-of-sight direction determining unit 107 sets whether or not the calibrated line-of-sight direction and the direction of the gaze determination target are similar on the basis of a preset threshold value. The threshold value is set on the basis of the user's current line-of-sight direction and information indicating the surrounding situation. For example, the threshold value is set to a large value when it is determined that a target visually recognized by the user is positioned close to the user, and is set to a small value when it is determined that a target visually recognized by the user is positioned far from the user.

Next, a hardware configuration example of the line-of-sight direction calibration device 100 will be described.

Figure 2A:
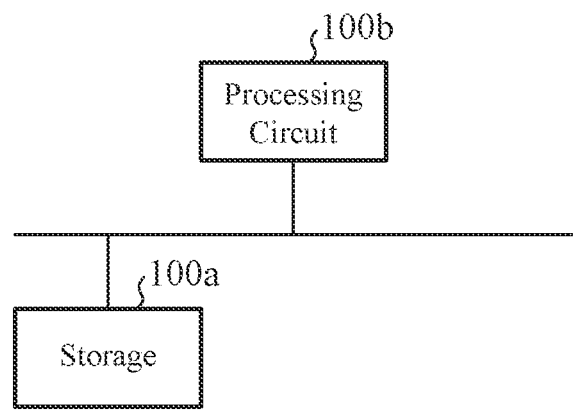
FIGS. 2A and 2B are diagrams each illustrating an exemplary hardware configuration of the line-of-sight direction calibration device according to the first embodiment.
Figure 2B:
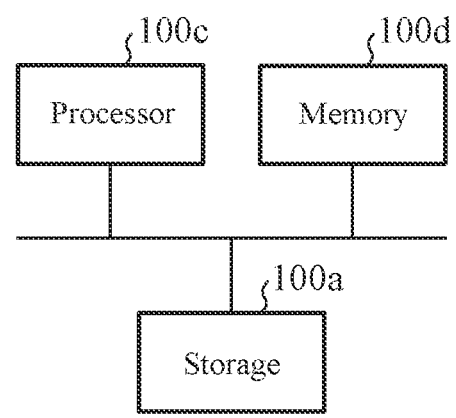

FIGS. 2A and 2B are diagrams each illustrating an exemplary hardware configuration of the line-of-sight direction calibration device 100 according to the first embodiment.

The calibration parameter storing unit 106a and the line-of-sight direction storing unit 106b in the line-of-sight direction calibration device 100 are implemented by a storage 100a. Each of the functions of the calibration information acquiring unit 101, the sample acquiring unit 102, the calibration model generating unit 103, the calibration parameter calculating unit 104, the calibrated value calculating unit 105, and the line-of-sight direction determining unit 107 in the line-of-sight direction calibration device 100 are implemented by a processing circuit. That is, the line-of-sight direction calibration device 100 includes a processing circuit for implementing the above functions. The processing circuit may be a processing circuit 100b which is dedicated hardware as illustrated in FIG. 2A, or may be a processor 100c for executing programs stored in a memory 100d as illustrated in FIG. 2B.

In the case where the calibration information acquiring unit 101, the sample acquiring unit 102, the calibration model generating unit 103, the calibration parameter calculating unit 104, the calibrated value calculating unit 105, and the line-of-sight direction determining unit 107 are implemented by dedicated hardware as illustrated in FIG. 2A, the processing circuit 100b corresponds to, for example, a single circuit, a composite circuit, a programmed processor, a parallel-programmed processor, an application specific integrated circuit (ASIC), a field-programmable gate array (FPGA), or a combination thereof. The functions of the calibration information acquiring unit 101, the sample acquiring unit 102, the calibration model generating unit 103, the calibration parameter calculating unit 104, the calibrated value calculating unit 105, and the line-of-sight direction determining unit 107 may be separately implemented by processing circuits, or may be implemented collectively by a single processing circuit.

In the case where the calibration information acquiring unit 101, the sample acquiring unit 102, the calibration model generating unit 103, the calibration parameter calculating unit 104, the calibrated value calculating unit 105, and the line-of-sight direction determining unit 107 correspond to the processor 100c as illustrated in FIG. 2B, the function of each unit are implemented by software, firmware, or a combination of software and firmware. The software or the firmware is described as a program and stored in the memory 100d. The processor 100c reads out and executes the program stored in the memory 100d and thereby implements the functions of the calibration information acquiring unit 101, the sample acquiring unit 102, the calibration model generating unit 103, the calibration parameter calculating unit 104, the calibrated value calculating unit 105, and the line-of-sight direction determining unit 107. That is, the calibration information acquiring unit 101, the sample acquiring unit 102, the calibration model generating unit 103, the calibration parameter calculating unit 104, the calibrated value calculating unit 105, and the line-of-sight direction determining unit 107 include the memory 100d for storing a program that is executed by the processor 100c results in execution of steps illustrated in FIGS. 7 and 8 described later. It can also be said that these programs cause a computer to execute procedures or methods of the calibration information acquiring unit 101, the sample acquiring unit 102, the calibration model generating unit 103, the calibration parameter calculating unit 104, the calibrated value calculating unit 105, and the line-of-sight direction determining unit 107.

Here, the processor 100c may be, for example, a central processing unit (CPU), a processing device, an arithmetic device, a processor, a microprocessor, a microcomputer, a digital signal processor (DSP), or the like.

The memory 100d may be a nonvolatile or volatile semiconductor memory such as a random access memory (RAM), a read only memory (ROM), a flash memory, an erasable programmable ROM (EPROM), an electrically EPROM (EEPROM), a magnetic disk such as a hard disk or a flexible disk, or an optical disk such as a mini disk, a compact disc (CD), or a digital versatile disc (DVD).

Note that some of the functions of the calibration information acquiring unit 101, the sample acquiring unit 102, the calibration model generating unit 103, the calibration parameter calculating unit 104, the calibrated value calculating unit 105, and the line-of-sight direction determining unit 107 may be implemented by dedicated hardware and another part thereof is implemented by software or firmware. In this manner, the processing circuit in the line-of-sight direction calibration device 100 can implement the above functions by hardware, software, firmware, or a combination thereof.

Next, details of the calibration model generating unit 103 and the calibration parameter calculating unit 104 will be described. First, a coordinate system of three-dimensional coordinates used as a reference for calibration used in the line-of-sight direction calibration device 100 will be described.

Figure 3:
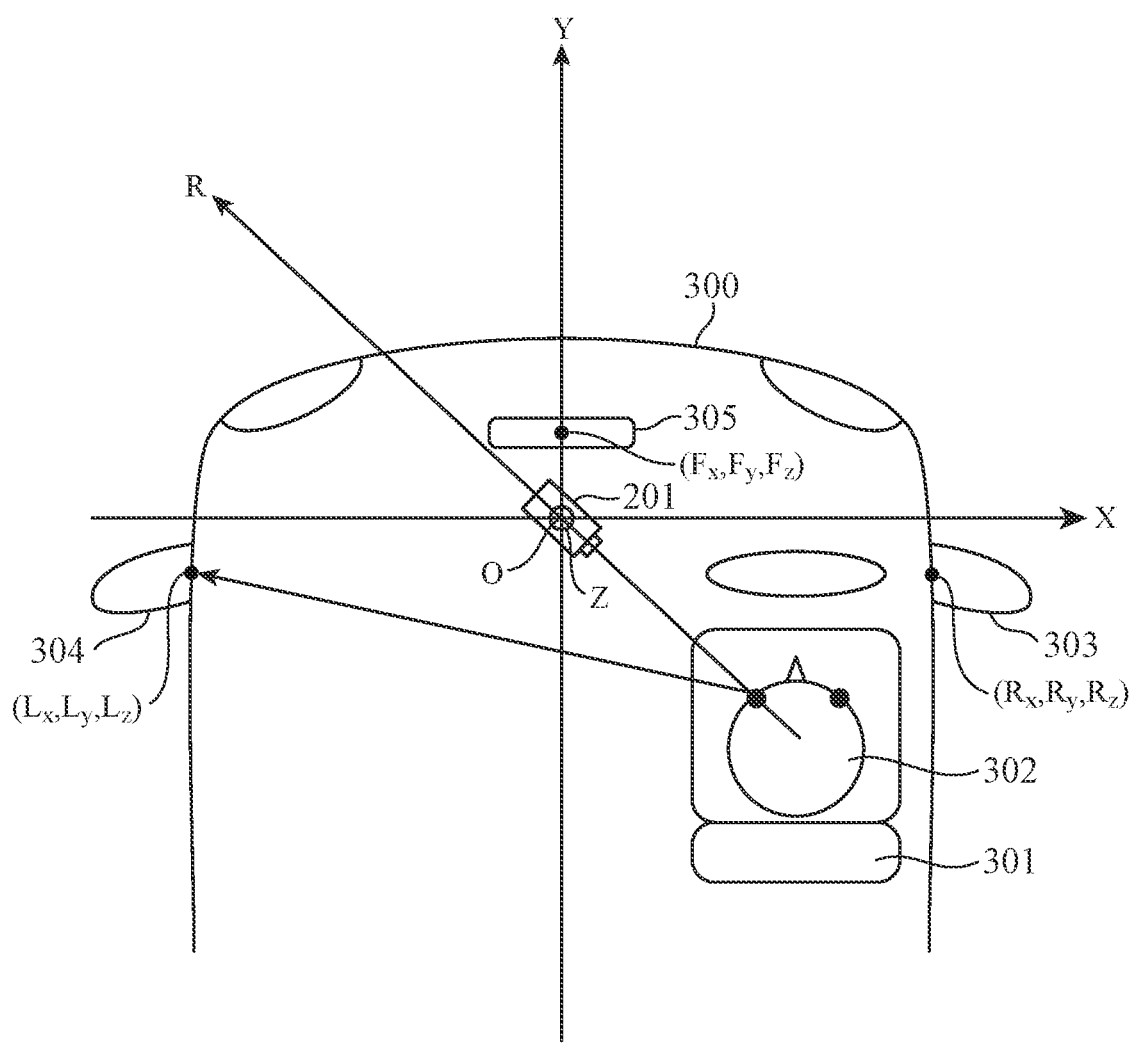
FIG. 3 is a diagram illustrating three-dimensional coordinates used in the line-of-sight direction calibration device according to the first embodiment.

FIG. 3 is a diagram illustrating three-dimensional coordinates used in the line-of-sight direction calibration device 100 according to the first embodiment. In FIG. 3, a case will be described as an example in which the line-of-sight direction calibration device 100 calibrates the line-of-sight direction of a driver of the vehicle.

The coordinate axes are the X axis in the width direction of a vehicle 300, the Y axis in the traveling direction of the vehicle 300, and the Z axis is a direction perpendicular to a road surface on which the vehicle 300 travels. The X axis is positive in a direction toward the right side of the traveling direction of the vehicle, and the Y axis is positive in a direction toward the traveling direction of the vehicle. The Z axis is positive in a direction upward from the road surface. The origin O of the three-dimensional coordinates is the center position of the line-of-sight measurement device 201 mounted on the vehicle 300. In FIG. 3, a reference direction of measurement in the line-of-sight measurement device 201 when projected onto the X-Y plane is indicated by the R axis on the X-Y plane. Note that since the rotation parameter (p) is unknown here as described above, the reference direction of the line-of-sight measurement device 201 is also unknown.

Note that the setting of the coordinate axes illustrated in FIG. 3 is an example, and thus the setting of the origin of the coordinate axes, the directions of the coordinate axes, etc. can be modified as needed.

A driver 302 is seated on a driver's seat 301 of the vehicle 300. A right side view mirror 303, a left side view mirror 304, and a rearview mirror 305 of the vehicle 300 are the gaze targets for calibration. For example, when a gaze instruction such as "please look at the left side view mirror" is given by a control unit (not illustrated) of the line-of-sight direction calibration device 100 before start of driving, the driver 302 gazes at the left side view mirror 304. A state, in which the line-of-sight direction of the driver 302 stays at a constant value after the gaze instruction, is regarded as a state in which the driver 302 is gazing at the gaze target for calibration. At this time, in order to facilitate the association between a line-of-sight direction and a gaze target for calibration, it is desirable to select the order of presentation of gaze targets so that the line of sight moves greatly vertically and horizontally. This facilitates detection of a section in which the line of sight moves greatly as a section in which the line-of-sight direction has moved between gaze targets for calibration. For example, presenting the right side view mirror 303, the left side view mirror 304, and the rearview mirror 305 in the order mentioned facilitates discrimination in the gaze determination of gaze targets for calibration than presenting them in the order of the right side view mirror 303, the rearview mirror 305, and the left side view mirror 304.

As another approach, the driver 302 may be regarded to be in a state of gazing at a gaze target for calibration by estimating a state of gazing at the left side view mirror 304 or the like when the driver 302 frequently pays attention for safety confirmation or the like when the vehicle 300 is traveling.

Next, processes of the calibration model generating unit 103 and the calibration parameter calculating unit 104 in the three-dimensional coordinates illustrated in FIG. 3 will be described with reference to FIGS. 4 and 5.

Figure 4:
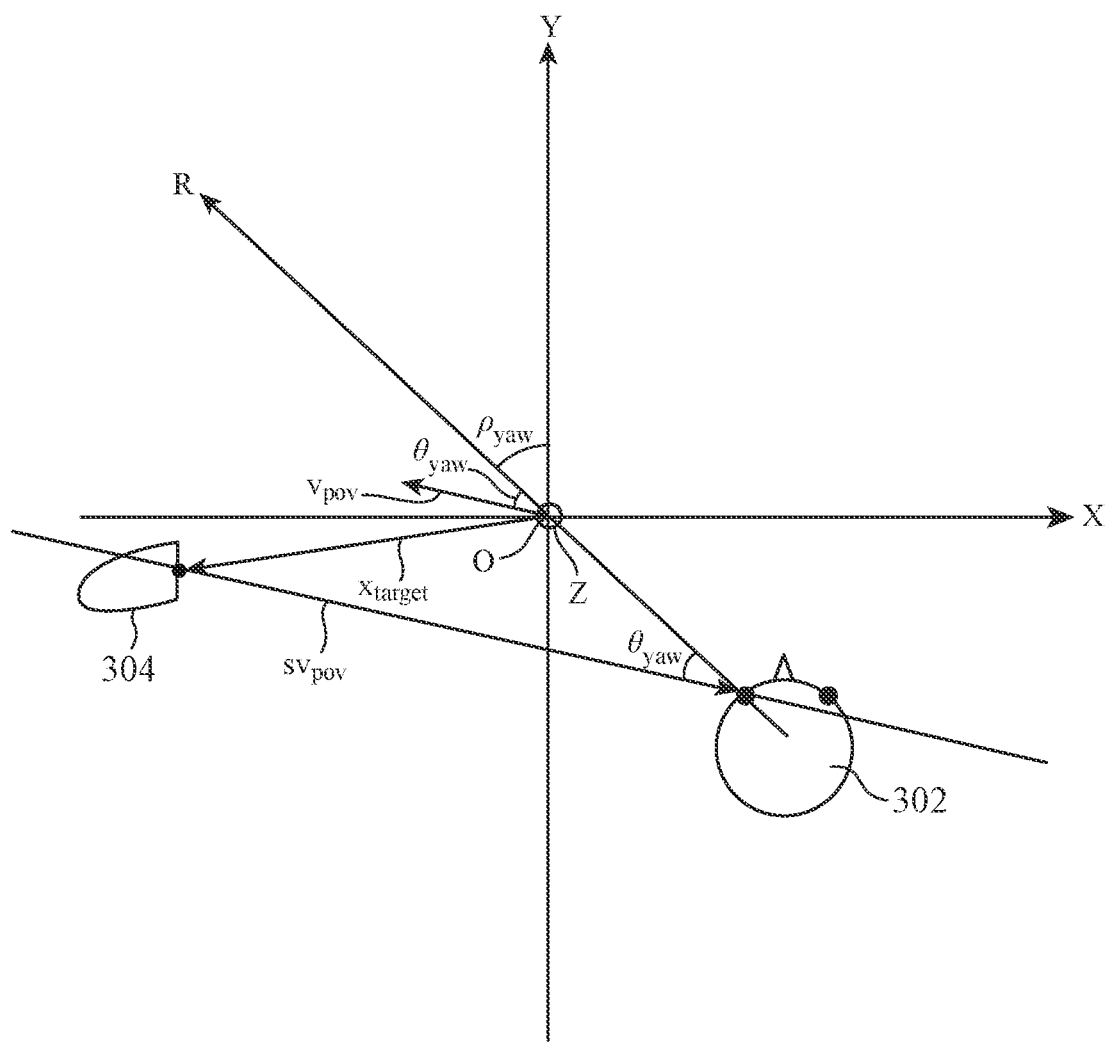
FIG. 4 is an explanatory diagram illustrating a process by a calibration model generating unit of the line-of-sight direction calibration device according to the first embodiment.
Figure 5:
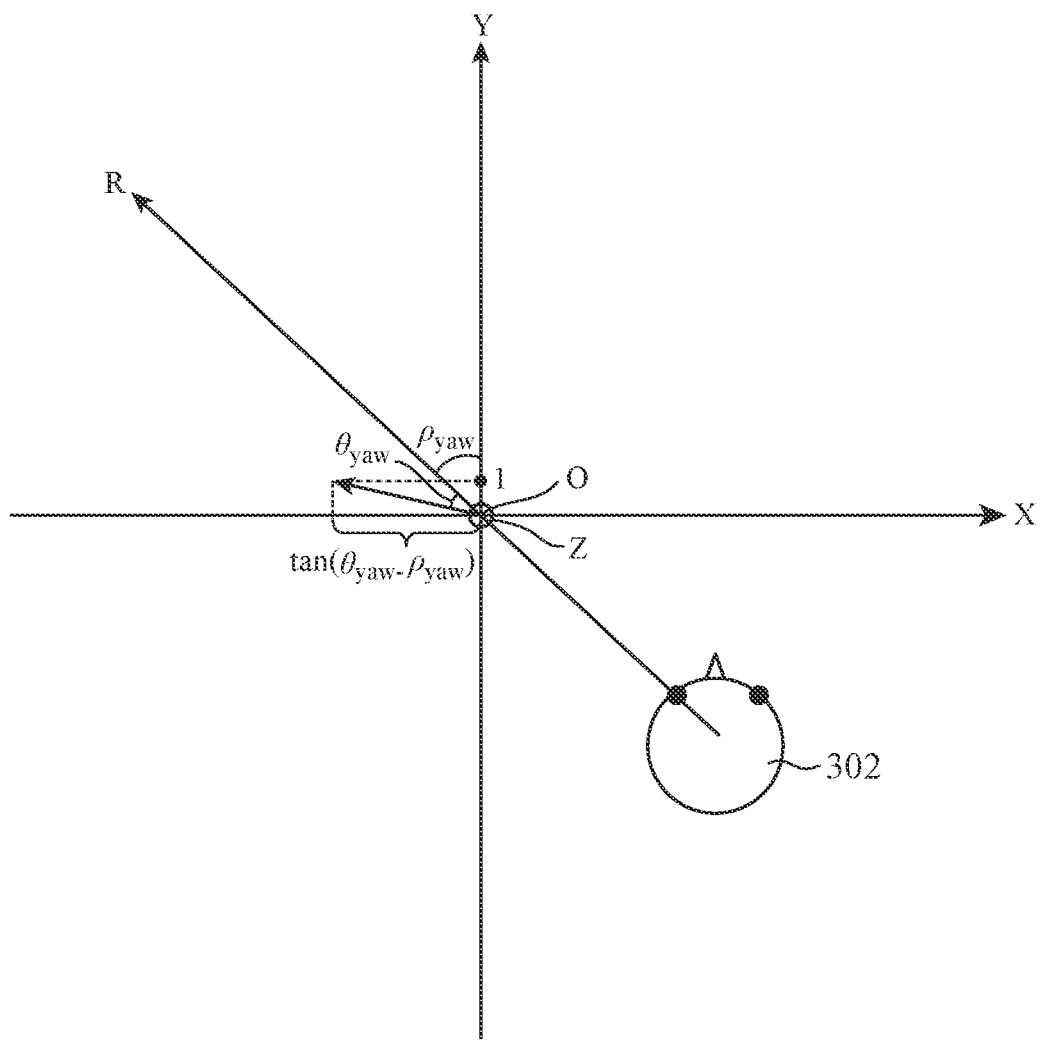
FIG. 5 is an explanatory diagram illustrating a process by a calibration model generating unit of the line-of-sight direction calibration device according to the first embodiment.

FIGS. 4 and 5 are an explanatory diagrams illustrating a process by the calibration model generating unit 103 of the line-of-sight direction calibration device 100 according to the first embodiment.

The calibration information acquiring unit 101 acquires three-dimensional coordinates ($R_X$, $R^Y$, $R^Z$) of the center point of the right side view mirror 303, three-dimensional coordinates ($L_X$, $L_Y$, $L_Z$) of the center point of the left side view mirror 304, and three-dimensional coordinates ($F_X$, $F_Y$, $F_Z$) of the center point of the rearview mirror 305, which are the gaze targets for calibration, and outputs the coordinates to the calibration model generating unit 103.

In FIGS. 4 and 5, the generation of a calibration model and the calculation of calibration parameters will be described by looking at an exemplary state in which the driver 302 is gazing at the left side view mirror 304.

FIG. 4 is a diagram illustrating the process of the calibration model generating unit 103 when the driver 302 gazes at the left side view mirror 304. In the example of FIG. 4, description will be given on the assumption that the calibration model generating unit 103 generates a calibration model indicating, as a user position, three-dimensional coordinates that is a candidate for the center position of the left eyeball of a user.

The calibration model generating unit 103 generates a calibration model indicating three-dimensional coordinates that is a candidate for the user position when the driver 302 is gazing at the left side view mirror 304 on the basis of the following equations (1) and (2).

$$\tilde{x}_{head}(s, \rho) = x_{target} + s v_{pov} \qquad (1)$$

$$v_{pov} = \begin{bmatrix} \tan(\theta_{yaw} - \rho_{yaw}) \\ 1 \\ \tan(\theta_{pitch} - \rho_{pitch}) \end{bmatrix} \qquad (2)$$

Expression $\tilde{x}_{head}$ in equation (1) is a calibration model and represents a position in a three-dimensional coordinate space that is a candidate for the user position, and more specifically, it represents a point on a straight line that virtually exists in the three-dimensional space. Value $x_{target}$ is a position vector representing the position of a gaze target for calibration in the three-dimensional space. In FIG. 4, $x_{target}$ is a position vector representing the center position of the left side view mirror 304 in the three-dimensional space. Value s is a position parameter and is a real number. Value $v_{pov}$ is a direction vector indicating a line-of-sight direction (hereinafter referred to as a line-of-sight direction vector) when the driver 302 is gazing at the left side view mirror 304.

Equation (2) represents components of a line-of-sight direction vector $v_{pov}$ in equation (1). Angle θ in equation (2) represents an angle which is output from the line-of-sight measurement device 201 and indicates a measurement value in the line-of-sight direction. Angle $θ_{yaw}$ is a measurement value in the line-of-sight direction in the X-Y plane direction. Angle $θ_{pitch}$ is an angle indicating a measurement value in the line-of-sight direction on the Y-Z plane.

In addition, ρ in equation (2) is a rotation parameter, and is an angle formed by a reference direction of measurement by the line-of-sight measurement device 201 and a reference direction (here, the Y axis) of a calibrated line of sight. Angle $ρ_{yaw}$ represents an angle formed by the reference direction of measurement in the line-of-sight measurement device 201 and the Y axis, and indicates the rotation angle about the Z axis. Angle $ρ_{pitch}$ represents an angle formed by the reference direction of measurement in the line-of-sight measurement device 201 when projected onto the Y-Z plane and the Y axis.

In the example of FIG. 4, $θ_{yaw}$ and $ρ_{yaw}$ are illustrated.

Note that the above-described formulation of equation (1) of the calibrating process is an example for the purpose of explanation.

FIG. 5 is a diagram illustrating the x component of the line-of-sight direction vector $v_{pov}$. In FIG. 5, $θ_{yaw}$ is determined so that a clockwise direction, centered at the origin O with the R axis as a starting point, has a positive value. Therefore, $θ_{yaw}<0$ holds for $θ_{yaw}$ in FIG. 5. Furthermore, $ρ_{yaw}$ is determined so that a clockwise direction, centered at the origin O with the R axis as a starting point, has a positive value. Therefore, $ρ_{yaw}>0$ holds for $ρ_{yaw}$ in FIG. 5. If the signs of $θ_{yaw}$ and $ρ_{yaw}$ are determined as described above, and they component of the line-of-sight direction vector $v_{pov}$ is determined as "1," the x component is represented by tan $(θ_{yaw}-ρ_{yaw})$ as illustrated in FIG. 5. Note that the above definition can be applied regardless of whether the user position is on the left, the right, or in the center with respect to the line-of-sight measurement device 201.

Although not illustrated, the z component of the line-of-sight direction vector $v_{pov}$ is similarly represented using $θ_{pitch}$ and $ρ_{pitch}$.

The calibration model generating unit 103 executes the above-described process for multiple times while the driver 302 is gazing at the left side view mirror 304 to generate multiple calibration models $\tilde{x}_{head}$ indicating three-dimensional coordinates that are candidates for the user position. Then the line-of-sight direction calibration device 100 instructs the driver 302 to gaze at the right side view mirror 303, and the calibration model generating unit 103 generates multiple calibration models $\tilde{x}_{head}$ indicating three-dimensional coordinates that are candidates for the user position while the driver 302 is gazing at the right side view mirror 303. Subsequently, the line-of-sight direction calibration device 100 instructs the driver 302 to gaze at the rearview mirror 305, and the calibration model generating unit 103 generates multiple calibration models $\tilde{x}_{head}$ indicating three-dimensional coordinates that are candidates for the user position while the driver 302 is gazing at the rearview mirror 305.

With the calibration model generating unit 103 generating the multiple calibration models $\tilde{x}_{head}$ for the single gaze target for calibration, the calibration parameter calculating unit 104 calculates the most likely user position on the basis of a process described later. The calibration model generating unit 103 outputs, to the calibration parameter calculating unit 104, the multiple calibration models $\tilde{x}_{head}$ for the state in which the driver 302 is gazing at the right side view mirror 303, the multiple calibration models $\tilde{x}_{head}$ for the state in which the driver 302 is gazing at the left side view mirror 304, and the multiple calibration models $\tilde{x}_{head}$ for the state in which the driver 302 is gazing at the rearview mirror 305.

The calibration parameter calculating unit 104 estimates the most likely user position from the following expression (3) using the multiple calibration models $\tilde{x}_{head}$ input thereto.

$$\min_{s,ρ,\tilde{x}}(\tilde{x}_{head,i}(s_i,ρ)-\tilde{x})^2 \qquad (3)$$

In expression (3), $\tilde{x}_{head,i}$ represents a candidate for the user position estimated from an i-th calibration model $\tilde{x}_{head}$, and $\tilde{x}$ represents the maximum likelihood estimate of the user position.

Expression (3) presents an optimization problem for calculating, as the user position, a point having the highest likelihood in two norms from the candidates for the user position indicated by the calibration models generated from equations (1) and (2). The optimization problem is linear with respect to the position parameter s and the user position $\tilde{x}$ but is nonlinear with respect to the rotation parameter ρ. Therefore, it is possible to efficiently solve the problem by, for example, searching the minimal value for ρ by dichotomizing search and calculating s and $\tilde{x}$ for each ρ by the least squares method.

From the above process, the calibration parameter calculating unit 104 estimates the most likely user position of the driver 302 in which fluctuations in the line of sight of the driver 302 are also considered. The calibration parameter calculating unit 104 calculates, as calibration parameters, the rotation parameter ρ and the maximum likelihood estimate $\tilde{x}$ of the user position that are specified by solving the optimization problem. The calibration parameter calculating unit 104 either stores the calculated calibration parameters in the calibration parameter storing unit 106a or directly outputs to the calibrated value calculating unit 105.

With the above processes, the line-of-sight direction calibration device 100 can acquire parameters necessary for calibration of the line-of-sight direction from the three-dimensional coordinates of each of the gaze targets for calibration and the line-of-sight direction when the driver 302 is gazing at each of the gaze targets for calibration.

Figure 6:
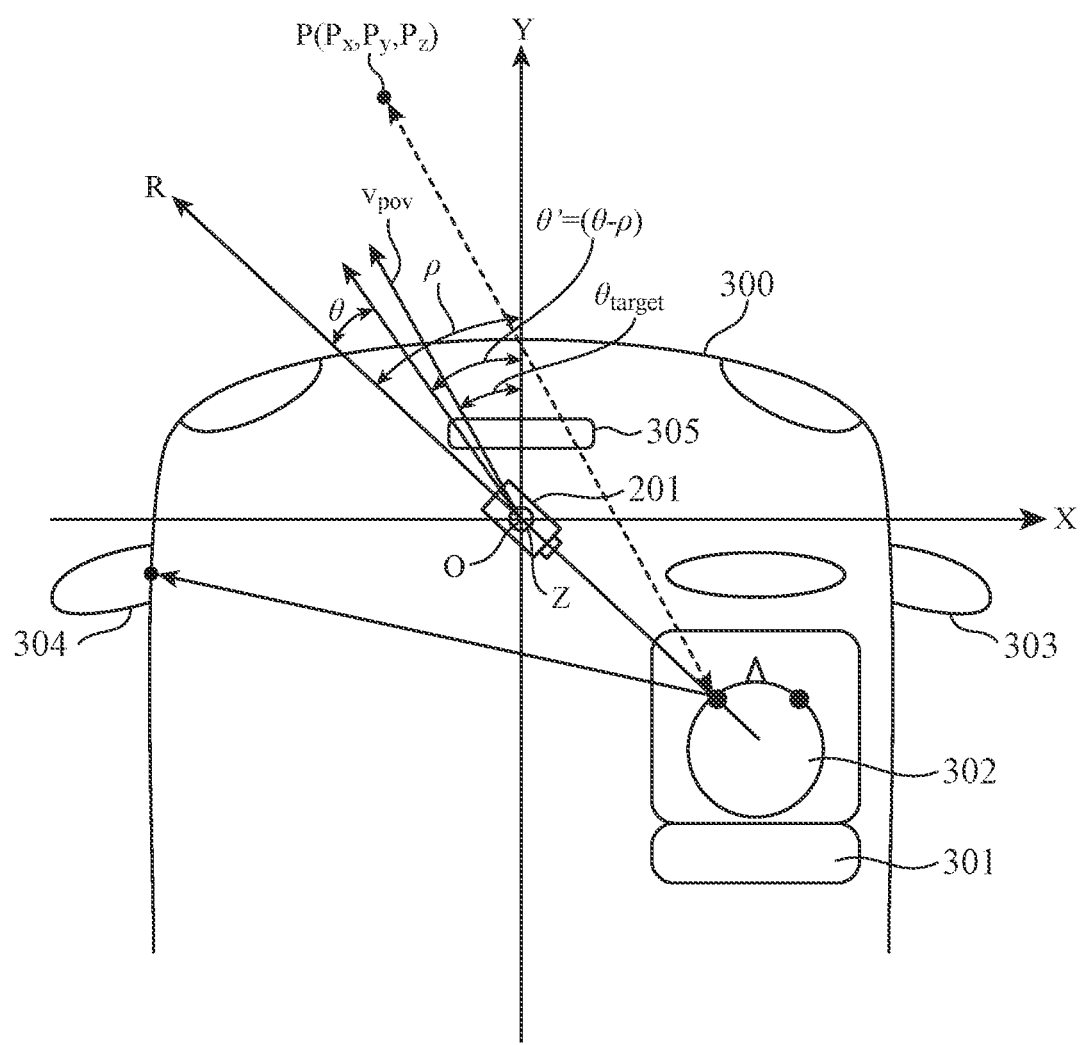
FIG. 6 is an explanatory diagram illustrating a calculation example of a calibrated value calculating unit of the line-of-sight direction calibration device according to the first embodiment.

FIG. 6 is an explanatory diagram illustrating exemplary processes of the calibrated value calculating unit 105 and the line-of-sight direction determining unit 107 of the line-of-sight direction calibration device 100 according to the first embodiment.

The calibrated value calculating unit 105 calculates a calibrated line-of-sight direction θ'=(θ−ρ) with respect to the line-of-sight direction θ input from the sample acquiring unit 102. The calibrated value calculating unit 105 stores the calculated calibrated line-of-sight direction θ' in the line-of-sight direction storing unit 106 or outputs it to the line-of-sight direction determining unit 107.

The line-of-sight direction determining unit 107 derives a line-of-sight direction vector $v_{pov}$ from the above equation (1) on the basis of three-dimensional coordinates (Px, Py, Pz) of a gaze determination target P input via the input device 202 and the user positions $\tilde{x}$ stored in the calibration parameter storing unit 106a. The line-of-sight direction determining unit 107 calculates the direction of the gaze determination target P, $θ_{target}$=arctan $(v_{pov})$, in a yaw-pitch space from the obtained line-of-sight direction vector $v_{pov}$. The line-of-sight direction determining unit 107 determines that the user has been viewing the gaze determination target P if the angular difference between the calibrated line-of-sight direction θ' input from the calibrated value calculating unit 105 and the direction $\theta_{target}$ of the gaze determination target P in the yaw-pitch space is less than a threshold value.

The calibrated value calculating unit 105 and the line-of-sight direction determining unit 107 may perform the following process.

The calibrated value calculating unit 105 derives the line-of-sight direction vector $v_{pov}$ from the above equation (2) on the basis of the line-of-sight direction θ input from the sample acquiring unit 102 and the rotation parameters ρ stored in the calibration parameter storing unit 106a. The calibrated value calculating unit 105 substitutes the derived line-of-sight direction vector $v_{pov}$ and the user position x̃ in the above equation (1) and rearranges the equation after the substitution to obtain the following equation (1a).

$$x_{target} = x_{head} - sv_{pov} \tag{1a}$$

This $x_{target}$ represents a straight line indicating the calibrated line-of-sight direction based on of the measured line-of-sight direction θ and the calibration parameters. The calibrated value calculating unit 105 outputs the acquired straight line $x_{target}$ to the line-of-sight direction determining unit 107.

The line-of-sight direction determining unit 107 calculates the distance from three-dimensional coordinates (Px, Py, Pz) of a gaze determination target P to the straight line $x_{target}$. In a case where the calculated distance is within a threshold value, the line-of-sight direction determining unit 107 determines that the user has been looking at the gaze determination target P.

Note that the threshold value for the line-of-sight direction determining unit 107 to determine whether or not the user is visually recognizing the gaze determination target P may be set on the basis of the distance between the gaze determination target P and the driver 302. For example, the threshold value is set continuously so that the threshold value increases as the distance between the gaze determination target P and the driver 302 decreases and that the threshold value decreases as the distance between the gaze determination target P and the driver 302 increases. Furthermore, the threshold value is not required to vary continuously depending on the distance between the gaze determination target P and the driver 302, and the threshold value may be set to be small in a case where the distance between the gaze determination target P and the driver 302 is within a preset distance, and in a case where the distance between the gaze determination target P and the driver 302 is longer than the preset distance, the threshold value may be set to be large.

In this manner, by setting the threshold value depending on the distance between the gaze determination target P and the driver 302, the line-of-sight direction determining unit 107 can determine the line-of-sight direction in consideration of a shift in the line-of-sight direction when the driver 302 is visually recognizing a point close to the driver 302 and a shift in the line-of-sight direction when the driver 302 visually recognizing a point far from the driver 302.

Note that although an example has been described in which the threshold value for determining whether or not the user is visually recognizing the gaze determination target is set on the basis of the distance between the gaze determination target P and the driver 302, the threshold value may be set on the basis of other conditions.

Next, the operation of the line-of-sight direction calibration device 100 will be described.

Hereinafter, the operation of the line-of-sight direction calibration device 100 will be described separately as operation of performing a calibration parameter calculating process and operation of performing a line-of-sight direction calibrating process and a line-of-sight direction determining process.

First, the calibration parameter calculating process will be described with reference to the flowchart in FIG. 7.

Figure 7:
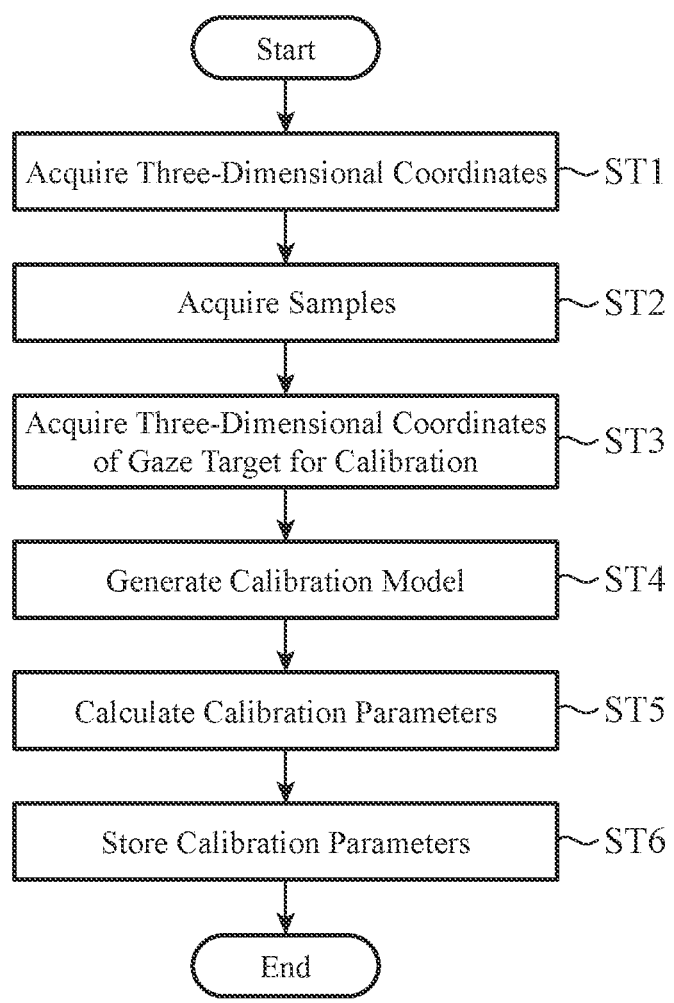
FIG. 7 is a flowchart illustrating an operation of calibration parameters calculating process of the line-of-sight direction calibration device according to the first embodiment.

FIG. 7 is a flowchart illustrating the operation of the calibration parameter calculating process by the line-of-sight direction calibration device 100 according to the first embodiment.

The calibration information acquiring unit 101 acquires three-dimensional coordinates of a gaze target for calibration (step ST1). The calibration information acquiring unit 101 outputs the acquired three-dimensional coordinates of the gaze target for calibration to the calibration model generating unit 103. Here, information for instructing the user which gaze target for calibration to gaze at is output from a speaker (not illustrated), a display (not illustrated), or the like. When the user gazes at the specified gaze target for calibration, the sample acquiring unit 102 acquires a sample indicating the line-of-sight direction of the user gazing at the gaze target for calibration from the line-of-sight measurement device 201, and outputs the sample to the calibration model generating unit 103 (step ST2).

The calibration model generating unit 103 associates and acquires the three-dimensional coordinates of the gaze target for calibration acquired in step ST1 and the gaze target for calibration that corresponds to the sample acquired by the sample acquiring unit 102 (step ST3). The calibration model generating unit 103 generates multiple calibration models indicating three-dimensional coordinates that is a candidate for the user position from the three-dimensional coordinates of the gaze target for calibration obtained in step ST3 and the sample acquired in step ST2 on the basis of the above equations (1) and (2) (step ST4). The calibration model generating unit 103 outputs the calibration model generated in step ST4 to the calibration parameter calculating unit 104.

The calibration parameter calculating unit 104 calculates, as calibration parameters, the rotation parameter ρ and the maximum likelihood estimate x̃ of the user position on the basis of the calibration models generated in step ST4 (step ST5). The calibration parameter calculating unit 104 stores the calculated calibration parameters in the calibration parameter storing unit 106a (step ST6) and terminates the process.

Next, the line-of-sight direction calibrating process and the line-of-sight direction determining process will be described with reference to the flowchart in FIG. 8.

Figure 8:
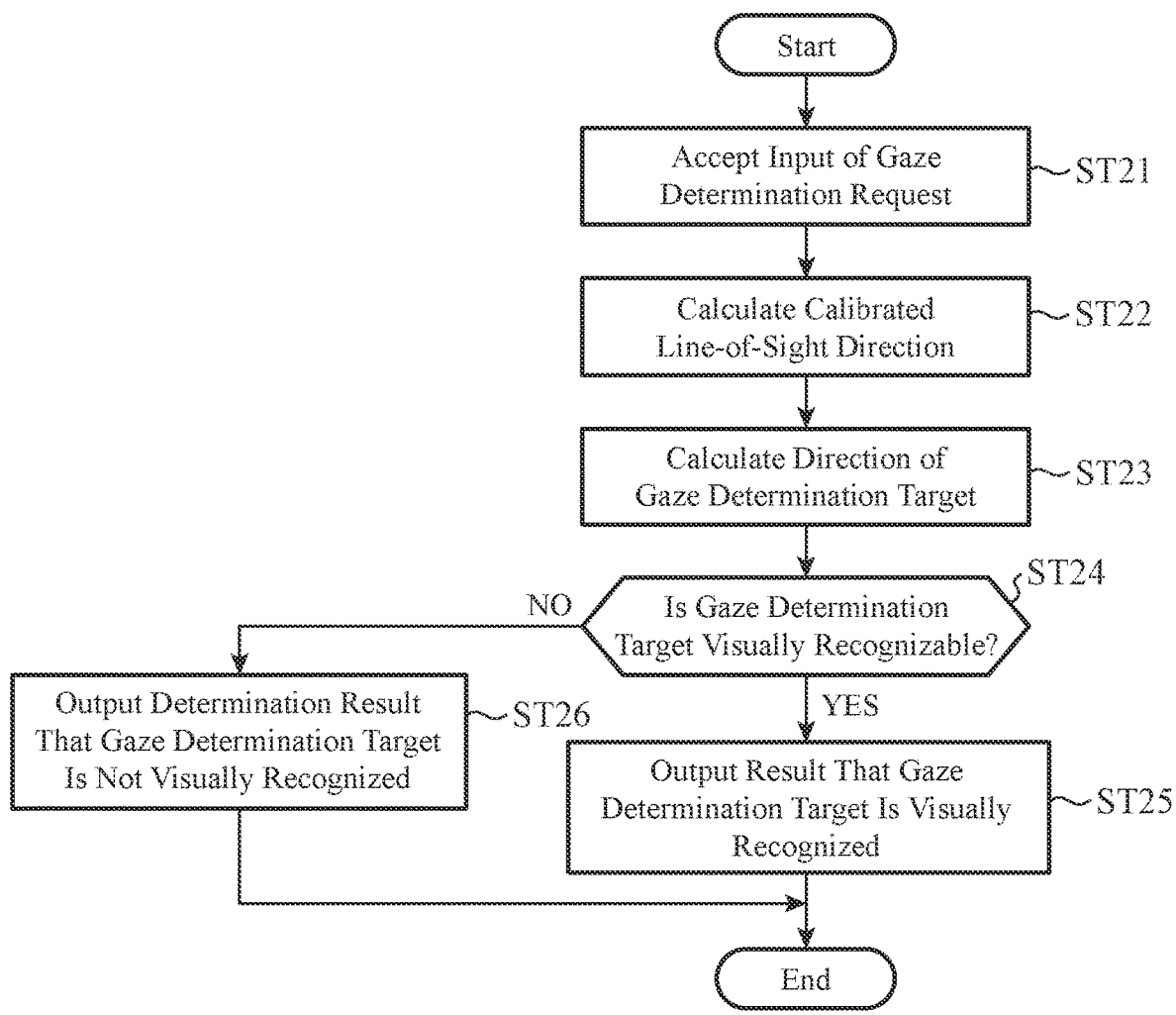
FIG. 8 is a flowchart illustrating an operation of a line-of-sight direction calibrating process and a line-of-sight direction determining process of the line-of-sight direction calibration device according to the first embodiment.

FIG. 8 is a flowchart illustrating the operation of the line-of-sight direction calibrating process and the line-of-sight direction determining process of the line-of-sight direction calibration device 100 according to the first embodiment.

When a determination request whether a gaze determination target is being gazed at is input via the input device 202 (step ST21), the calibrated value calculating unit 105 calculates a calibrated line-of-sight direction with respect to the sample line-of-sight direction acquired by the sample acquiring unit 102 (step ST22). The calibrated value calculating unit 105 outputs the calculated calibrated line-of-sight direction to the line-of-sight direction determining unit 107. The line-of-sight direction determining unit 107 calculates the direction of the gaze determination target (step ST23). The line-of-sight direction determining unit 107 determines whether or not the user is visually recognizing the gaze determination target on the basis of the calibrated line-of-sight direction calculated in step ST22 and the gaze determination target calculated in step ST23 (step ST24).

If the user is visually recognizing the gaze determination target (step ST24: YES), the line-of-sight direction determining unit 107 outputs a result indicating that the user is visually recognizing the gaze determination target (step ST25), and terminates the process.

On the other hand, if the user is not visually recognizing the gaze determination target (step ST24: NO), the line-of-sight direction determining unit 107 outputs a determination result indicating that the user is not visually recognizing the gaze determination target (step ST26), and terminates the process.

Figure 9:
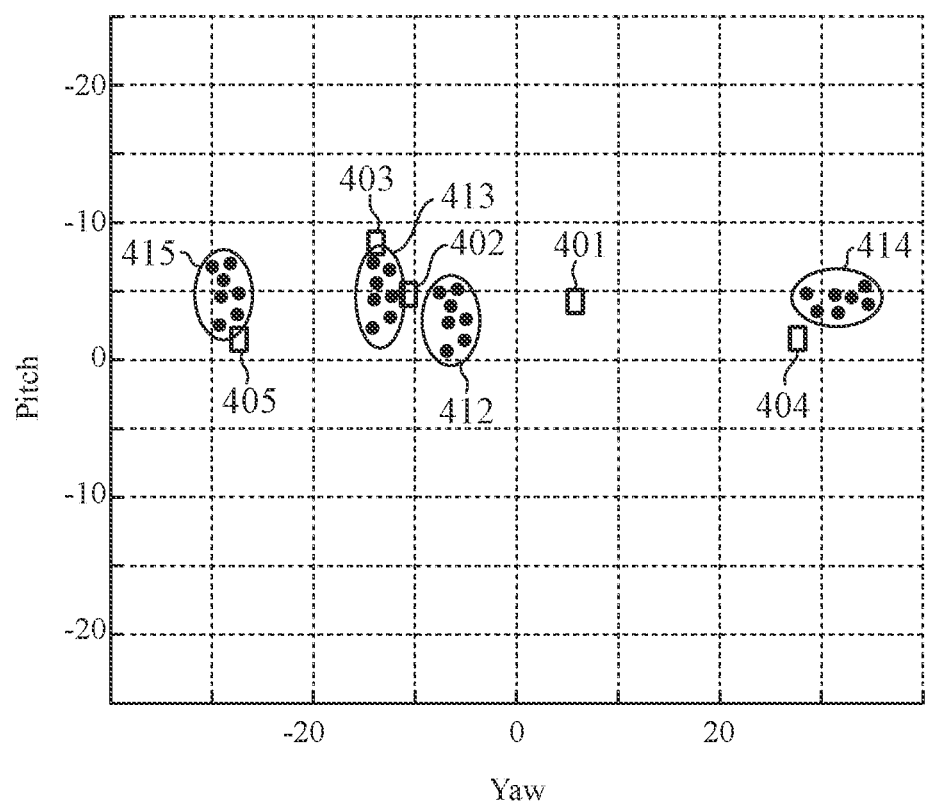
FIG. 9 is a diagram illustrating a result of a calibrating process of the line-of-sight direction calibration device according to the first embodiment.

FIG. 9 is a diagram illustrating a result of the calibrating process of the line-of-sight direction calibration device 100 according to the first embodiment.

In FIG. 9, a result of performing the above-described line-of-sight direction calibrating process is illustrated using accessories in the vehicle as gaze targets for calibration. As accessories of the vehicle, a case is illustrated in FIG. 9 in which the line-of-sight measurement device 201, the rearview mirror 305, the right side view mirror 303, and the left side view mirror 304 are gaze targets.

In FIG. 9, the horizontal axis indicates the position in the line-of-sight direction in the vehicle width direction, and the vertical axis indicates the position in the line-of-sight direction perpendicular to a road surface on which the vehicle travels. A rectangular area 401 indicates a front position of the user. Rectangular areas 402 to 405 indicate positions in the calibrated line-of-sight direction in a case where each accessory of the vehicle is used as a gaze target for calibration. Results 412 to 415 indicate the position of the user's line-of-sight direction when each accessory of the vehicle as a gaze target for calibration is gazed at. It is illustrated in FIG. 9 that the rectangular areas representing the positions of calibrated line-of-sight directions converge to a result that corresponds thereto by the calibrating process by the line-of-sight direction calibration device 100.

Note that, in FIG. 9, a result 412 illustrates plots of line of sight vectors of the user when the user gazes at the line-of-sight measurement device 201. Likewise, a result 413, a result 414, and a result 415 illustrate plots of line of sight vectors of the user when the user gazes at the rearview mirror 305, the right side view mirror 303, and the left side view mirror 304, respectively.

A driver frequently visually recognizes vehicle accessories such as a rearview mirror or a side view mirror while the vehicle is travelling. Therefore, by setting vehicle accessories as gaze targets for calibration, it becomes possible to perform the line-of-sight direction calibrating process by an unconscious behavior such as the driver looking at the vehicle accessories while driving the vehicle or an inevitable behavior.

Technology of setting a reference in the line-of-sight direction and calibrating detection of the line-of-sight direction by a driver's behavior of looking at the vehicle accessories while driving the vehicle is disclosed in, for example, the following Reference Literature 1.

Reference Literature 1

JP 2010-30361 A

As described above, the line-of-sight direction calibration device 100 according to the first embodiment includes: the calibration information acquiring unit 101 for acquiring three-dimensional coordinates indicating the position of each gaze target for calibration for at least one gaze target for calibration; the sample acquiring unit 102 for acquiring multiple samples indicating a line-of-sight direction of a user; the calibration model generating unit 103 for generating multiple calibration models indicating three-dimensional coordinates that are candidates for a position of the user on the basis of the acquired three-dimensional coordinates and the acquired samples indicating the line-of-sight direction of the user gazing at each of the gaze targets for calibration; and the calibration parameter calculating unit 104 for calculating calibration parameters on the basis of the generated calibration models.

This enables calibration of a measurement error included in the line-of-sight direction measured for the line of sight directed to any point. It is also made possible to calculate the calibration parameters only from the line-of-sight direction and information of the gaze target for calibration. For this reason, for example, the calibration parameters can be calculated even when only a line-of-sight direction measurement value based on one imaging means is used, and thus the configuration is simplified, and the cost can be reduced as compared with the technology of using a distance meter for grasping the user position or the technology of using multiple imaging means.

In addition, the line-of-sight direction calibration device 100 according to the first embodiment includes: the calibrated value calculating unit 105 for calibrating the line-of-sight direction of the user acquired by the sample acquiring unit 102 on the basis of the calibration parameters calculated by the calibration parameter calculating unit 104, and calculating a calibrated line-of-sight direction; and the line-of-sight direction determining unit 107 for determining whether or not the user is visually recognizing the gaze determination target on the basis of the calculated calibrated line-of-sight direction and the calibration parameters calculated by the calibration parameter calculating unit 104.

This makes it possible to determine the user's line-of-sight direction directed to any point.

Note that in a case where the measurement characteristics of the line-of-sight measurement device 201 are also to be calibrated in the line-of-sight direction calibration device 100 according to the first embodiment described above, it suffices to transform the above equation (2) into the following equation (2a).

$$v_{pov} = \begin{bmatrix} \tan(f(\alpha, \theta_{yaw}) - \rho_{yaw}) \\ 1 \\ \tan(f(\alpha, \theta_{pitch}) - \rho_{pitch}) \end{bmatrix} \quad (2a)$$

In equation (2a), angle θ in equation (2) is replaced with f(α, θ). In equation (2a), the measurement characteristics of the line-of-sight measurement device 201 can be made a calibration target by optimizing the variable a in the function f.

In a case where the sensitivity of the sample acquiring unit 102 changes in the X, Y, and Z directions in the three-dimensional coordinates due to individual differences between users or individual differences of line-of-sight measurement devices 201, f(α, θ) in equation (2a) is replaced with αθ. As a result, the sensitivity of the measurement characteristics of the line-of-sight measurement device 201 can be calibrated simultaneously. Note that α in equation (2a) may be set separately for $\alpha_{yaw}$ and $\alpha_{pitch}$.

In the above-described line-of-sight direction calibration device 100 according to the first embodiment, the calibration parameter calculating unit 104 calculates the most likely user position as the calibration parameters from the expression (3) using the multiple calibration models $\bar{x}_{head,i}$ input thereto. In this process, the most likely user position may be calculated by adding weightings to the multiple calibration models $\tilde{x}_{head,i}$ used in the calibration depending on the reliability or the like of the values of the calibration models $\tilde{x}_{head,i}$. In a case where weightings are added to the calibration models $\tilde{x}_{head,i}$, the calibration models $\tilde{x}_{head,i}$ are replaced with $w_i \tilde{x}_{head,i}$.

For example in a case where measurement characteristics of the line-of-sight measurement device 201 exhibits a high measurement accuracy in the central part of the measurement range and a low measurement accuracy in the peripheral areas, weightings of calibration models $\tilde{x}_{head,i}$ of a gaze target located in or near the center of the measurement range are set to be large while weightings of calibration models $\tilde{x}_{head,i}$ of a gaze target located in peripheral areas of the measurement range are set to be small. This allows the calibration parameter calculating unit 104 in the line-of-sight direction calibration device 100 to suppress errors when calculating the most likely user position.

As another example of measurement characteristics of the line-of-sight measurement device 201, in a case where a gaze target for calibration is closer to the user position, the visual angle becomes larger as compared to a case where the gaze target for calibration having the same size is at a distant position, and thus it is assumed that measurement values in the line-of-sight direction vary greatly since a deviation from the center coordinates of the gaze target for calibration becomes large. If measurement values in the line-of-sight direction vary greatly, there is a disadvantage that it is more likely that the calibration model does not appropriately reflect the user position, thereby degrading the estimation accuracy of the calibration parameters. Therefore, it is desirable to reduce a weighting factor as variations in the line-of-sight direction increases by, for example, adding a weighting factor obtained by $w=\exp(-\sigma)$ where $\sigma$ is the standard deviation in the line-of-sight direction when the same gaze target for calibration is gazed at.

As another example, there are cases where a gaze target temporarily deviates from the field of view due to a saccade or other reasons even when the user keeps gazing at the same gaze target while the line-of-sight direction calibration device 100 is performing a calibration process. For determination whether the user is gazing at a gaze target, it is typical to discriminate between movement and retention of a line of sight and to thereby determine retention as a state of gazing. However, setting strict conditions for determining retention of a line-of-sight brings about a tradeoff between improvement in the selection accuracy of calibration models $\tilde{x}_{head,i}$ used in calibration and deterioration in the reliability of the calibration result due to the reduced number of calibration models $\tilde{x}_{head,i}$ used in the calibration. In such a situation, line-of-sight direction vectors for the same gaze target are statistically reviewed, and weightings for calibration models $\tilde{x}_{head,i}$ are reduced depending on the degree of deviation from the distribution of the line-of-sight direction vectors. This can ensure the accuracy and the reliability of the calibration result.

Note that although a case has been described in the above description in which weighting is continuously performed using the standard deviation 6 in the line-of-sight direction as a reference, a calibration model may be weighted discontinuously like in the case of a soft margin in a support vector machine (SVM).

Note that a case has been described in the above description in which the line-of-sight direction calibration device 100 calculates the calibrated line-of-sight direction for any point in a three-dimensional space. However, the line-of-sight direction calibration device 100 may calculate a calibrated line-of-sight direction for any point in a two-dimensional space that is a special case of a three-dimensional space.

Note that the present invention may include modifications of any component of each embodiment, or omission of any component of each embodiment within the scope of the present invention.

INDUSTRIAL APPLICABILITY

A line-of-sight direction calibration device according to the present invention is applicable to a system or the like that is required to accurately determine a line-of-sight direction of a user and to accurately grasp a target visually recognized by the user in a device including a display such as an in-vehicle device and a television.

REFERENCE SIGNS LIST

100: Line-of-sight direction calibration device,
101: Calibration information acquiring unit,
102: Sample acquiring unit,
103: Calibration model generating unit,
104: Calibration parameter calculating unit,
105: Calibrated value calculating unit,
106a: Calibration parameter storing unit,
106b: Line-of-sight direction storing unit,
107: Line-of-sight direction determining unit.

What is claimed is:

1. A line-of-sight direction calibration device comprising: processing circuitry
to acquire three-dimensional coordinates for at least one gaze target for calibration, the three-dimensional coordinates indicating a position of each gaze target for calibration and being based on a predetermined coordinate system;
to acquire multiple samples indicating a line-of-sight direction of a user, the multiple samples being based on an unknown coordinate system that does not have a correspondence relationship with the predetermined coordinate system;
to generate multiple calibration models indicating three-dimensional coordinates that are candidates for a position of the user on a basis of the acquired three-dimensional coordinates, the samples indicating the line-of-sight direction of the user gazing at each of the gaze targets for calibration, an unknown parameter indicating the correspondence relationship between the predetermined coordinate system and the unknown coordinate system; and
to calculate, as a calibration parameter, the unknown parameter and the position of the user on a basis of the generated calibration models.

2. The line-of-sight direction calibration device according to claim 1, in which the processing circuitry calibrates the obtained line-of-sight direction of the user on a basis of the calculated calibration parameter, and calculating a calibrated line-of-sight direction; and
determine whether or not the user is visually recognizing a gaze determination target on a basis of the calculated calibrated line-of-sight direction and the calculated calibration parameter.

3. The line-of-sight direction calibration device according to claim 2, wherein a threshold value for causing the processing circuitry to determine that the user is visually recognizing the gaze determination target is set on a basis of a distance between the user and the gaze determination target.

4. The line-of-sight direction calibration device according to claim 1, wherein the processing circuitry sets a measurement characteristic of the line-of-sight measurement device for measurement of the line-of-sight direction of the user as a calibration target.

5. The line-of-sight direction calibration device according to claim 1, wherein the processing circuitry adds a weight to the calibration models depending on a position in a measurement range of a measurement device that measures the line-of-sight direction of the user.

6. The line-of-sight direction calibration device according to claim 1, wherein the processing circuitry adds a weight to the calibration models depending on a degree of variation of the line-of-sight direction of the user for each of the gaze targets for calibration.

7. The line-of-sight direction calibration device according to claim 1, wherein the processing circuitry adds, for each line-of-sight direction of the user, a weight to the calibration models depending on a degree of deviation of the line-of-sight direction of the user from a distribution of the line-of-sight direction of the user in the gaze target for calibration, to which the line-of-sight direction of the user belongs.

8. A line-of-sight direction calibration method comprising the steps of:
    acquiring three-dimensional coordinates for at least one gaze target for calibration, the three-dimensional coordinates indicating a position of each gaze target for calibration and being based on a predetermined coordinate system;
    acquiring multiple samples indicating a line-of-sight direction of a user, the multiple samples being based on an unknown coordinate system that does not have a correspondence relationship with the predetermined coordinate system;
    generating multiple calibration models indicating three-dimensional coordinates that are candidates for a position of the user on a basis of the three-dimensional coordinates indicating the position of each of the gaze targets for calibration, the samples indicating the line-of-sight direction of the user gazing at each of the gaze targets for calibration, an unknown parameter indicating the correspondence relationship between the predetermined coordinate system and the unknown coordinate system; and
    calculating as a calibration parameter, the unknown parameter and the position of the user on a basis of the generated calibration models.

9. A non-transitory computer readable medium having stored therein a line-of-sight direction calibration program for causing a computer to execute:
    acquiring three-dimensional coordinates for at least one gaze target for calibration, the three-dimensional coordinates indicating a position of each gaze target for calibration and being based on a predetermined coordinate system;
    acquiring multiple samples indicating a line-of-sight direction of a user, the multiple samples being based on an unknown coordinate system that does not have a correspondence relationship with the predetermined coordinate system;
    generating multiple calibration models indicating three-dimensional coordinates that are candidates for a position of the user on a basis of the three-dimensional coordinates indicating the position of each of the gaze targets for calibration, the samples indicating the line-of-sight direction of the user gazing at each of the gaze targets for calibration, an unknown parameter indicating the correspondence relationship between the predetermined coordinate system and the unknown coordinate system; and
    calculating, as a calibration parameter, the unknown parameter and the position of the user on a basis of the generated calibration models.

* * * * *